United States Patent [19]
Collins

[11] Patent Number: 5,559,848
[45] Date of Patent: Sep. 24, 1996

[54] IMAGING SYSTEM FOR PLASTIC COMPONENTS

[75] Inventor: Theresa A. Collins, Park Ridge, Ill.

[73] Assignee: Wesley-Jessen Corporation, Des Plaines, Ill.

[21] Appl. No.: 291,219

[22] Filed: Aug. 16, 1994

[51] Int. Cl.⁶ .................................................. G01B 15/06
[52] U.S. Cl. .................................................. 378/58; 378/51
[58] Field of Search .................................................. 378/58

Primary Examiner—Craig E. Church
Attorney, Agent, or Firm—Brinks Hofer Gilson & Lione

[57] ABSTRACT

A system is provided for inspecting components, especially plastic components such as contact lens casting cup assemblies. A process for inspecting such components is also provided. The process comprises transmitting x-rays through the object to be inspected and then onto an image sensing means.

9 Claims, 2 Drawing Sheets

IMAGING SYSTEM FOR PLASTIC COMPONENTS

FIELD OF THE INVENTION

This invention relates to a system for imaging plastic components, in order to inspect the components for defects. Plastic components that can be inspected using this system are, for example, polypropylene contact lens mold assemblies or casting cups.

BACKGROUND OF THE INVENTION

A principle objective of this invention is to provide a non-destructive and efficient means for inspecting contact lens casting cups for edge quality, alignment fit, center thickness, roundness, prism, and a variety of other defects.

There are currently inspection systems capable of imaging the interior of plastic mold assemblies. These systems, however, are limited in scope and typically image on a macro scale (i.e., in inches). Consequently, there is a need for a more precise non-destructive means for inspecting plastic components for parameters such as those described above.

More specifically, there is a need for a means for imaging the interior of casting cups used for molding contact lenses. Previously, inspection methods for such casting cup assemblies related to whether or not the exterior physical dimensions were in accordance with specification. However, exterior dimensions held little statistical significance to the quality of the lens compared with interior dimensions. Lens quality is reflected in part by the presence or absence of edge defects, edge configuration, and center thickness. There is thus a need for an inspection system that can better assess these important attributes.

SUMMARY OF THE INVENTION

The novel inspection system of the present invention is predicated upon the surprising discovery that x-ray analysis can be utilized as a means for non-destructively inspecting the qualitative parameters of plastic components, e.g., molded polypropylene or polystyrene contact lens casting cups. Specifically, the imaging system of the present invention comprises:

a) image sensing means for sensing the image of a plastic object; and b) means for transmitting x-rays through the plastic object and onto the image sensing means.

The imaging system of the present invention saves time and money because it does not require dissection of inspected devices.

A detailed description of the present invention is set forth below. However, the embodiments described herein are merely illustrative; further embodiments will be apparent to those having ordinary skill in the art.

DETAILED DESCRIPTION OF THE INVENTION

This invention describes a new way to image assembled plastic components, utilizing x-ray analysis to non-destructively inspect pre-assembled plastic components, e.g., contact lens casting cups, for edge quality, alignment fit, center thickness, roundness, prism, and other defects. Examples of casting cups that can be inspected with the system of the present invention are shown in U.S. Pat. Nos. 5,271,874; 5,087,015; 5,071,101; and 4,955,580. Examples of plastics from which such components can be made include but are not limited to: polypropylene, polystyrene, polyethylene, polycarbonate, polyvinyl chloride, polymethylpentene, polymethyl methacrylate, and nylon.

Figure 1:
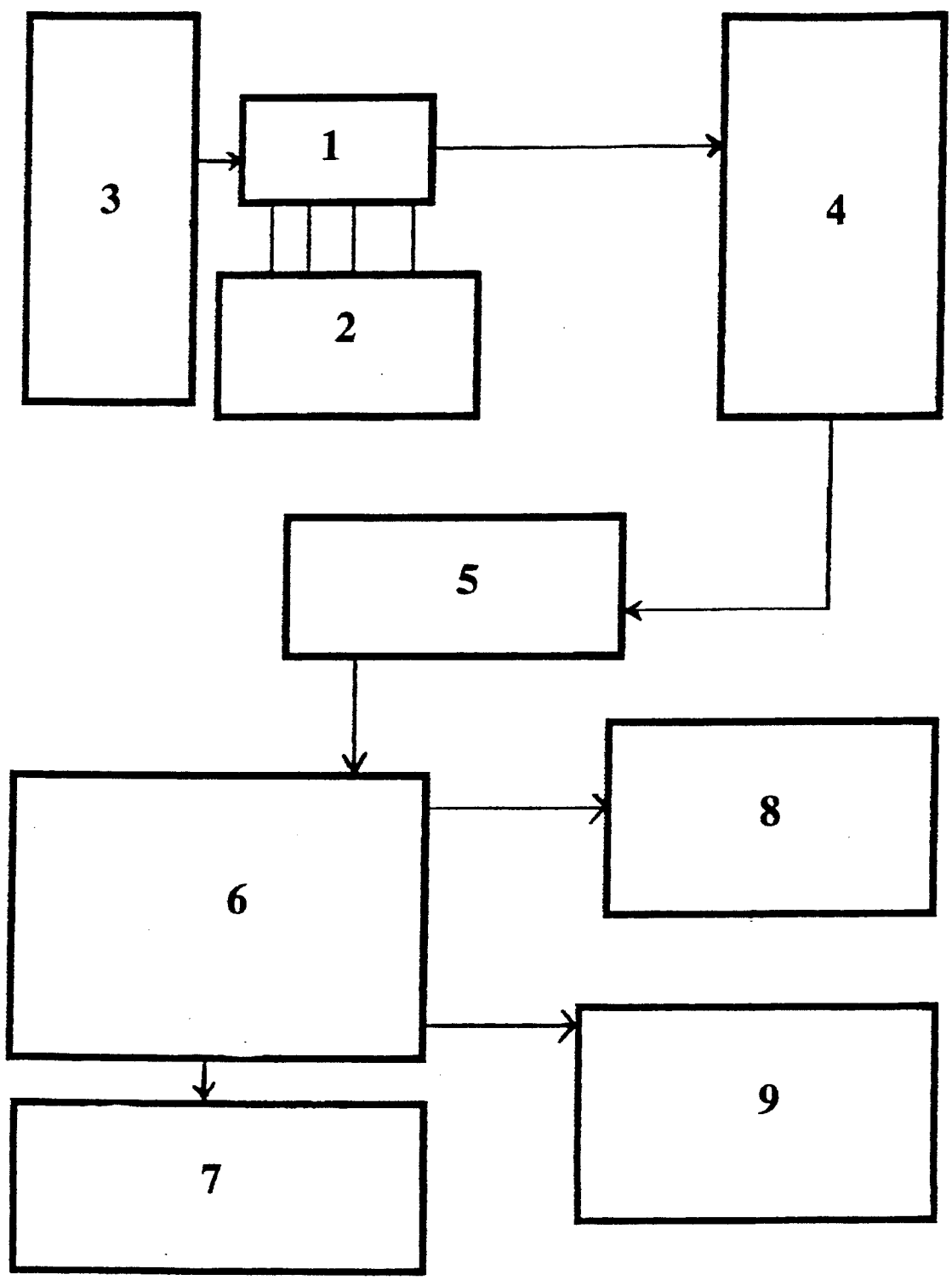
FIG. 1 is a schematic representation of the imaging process, showing the path of the x-rays through the plastic component, and the projection and magnification of the image through various stages of enhancement.
Figure 2:
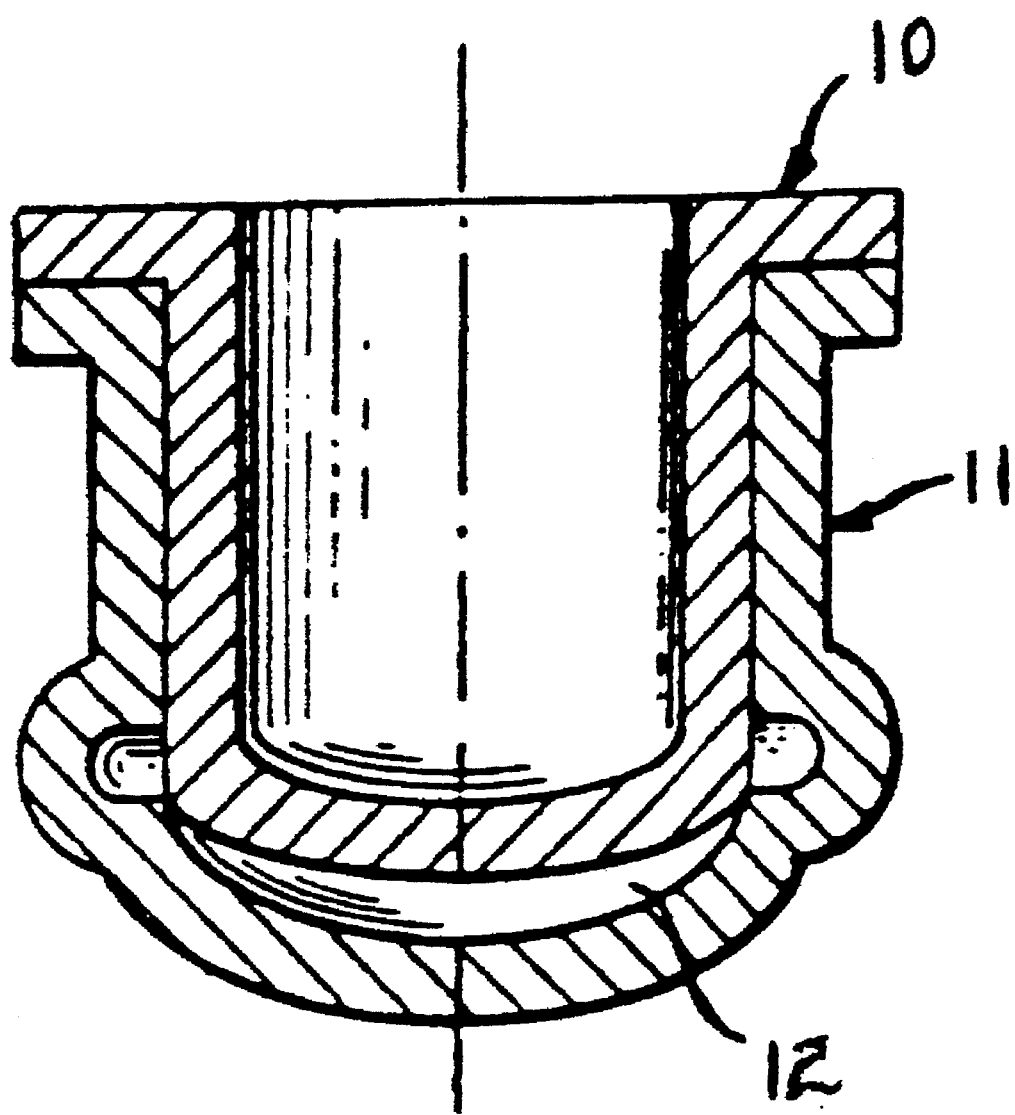
FIG. 2 is exemplary of the type of plastic components (i.e., contact lens mold assembies or casting cups) that can be inspected using this invention.

FIG. 2 is an example of the type of plastic components (contact lens mold assemby/casting cups) that can be inspected with this invention. As illustrated, when the male member (10), of the lens mold assembly is properly seated into the female member (11), a cavity (12) or the "alignment gap" is created. This gap or cavity is where the contact lens is formed. It should be noted that the dimensions and configuration of this particular example are unimportant to the utilization of this imaging system, and the invention should not be construed as limited thereby.

Preferred means of x-ray analysis include "real time x-ray analysis" and "near real-time x-ray analysis." Both involve using a microfocus x-ray source. "Real time x-ray analysis" is defined as a process by which an analysis (e.g., distance measurement, edge quality assessment, etc.) can be performed at the same time the part is being imaged. "Near real-time x-ray analysis" involves capturing a number of frames of the image (e.g., 64 or 128 frames), integrating the image, and then performing the analysis.

A "microfocus x-ray source" is a target (most frequently tungsten) which has a size of 50 microns or less and is important when looking at high geometric magnifications. The microfocus x-ray source can include an x-ray tube designed to convert electrical energy into radiation. The tube can consist of a cathode ray unit containing a tungsten filament target and a beryllium window. The heated filament casts off electrons and directs an electron stream at an anode or target and then the beam is focused. The focused beam is directed through a beryllium window and then onto an object (e.g., on a polypropylene casting cup). The typical size of the target ranges from 10–50 microns. 10 microns gives better resolution. In a preferred embodiment, after the component has been scanned by x-ray, the image is captured by a closed circuit television camera and sent to a software-driven image enhancer. The image enhancer refines and improves the x-ray image. The image can then be seen on a video monitor or transferred to a thermal printer.

More specifically, this invention can be better understood according to the following step by step description of the imaging process. The specific part numbers (P/N) for the examplary mechanical components of the following preferred embodiment are for the Lixi System HM2001, and are available from Lixi, Inc., Downers Grove, Ill.

The plastic mold assembly to be imaged is first placed on a stainless steel holder (1), which is then placed on the sample manipulator (2), here, Lixi P/N 50854. The sample manipulator can be equipped with a parts rotator such as Lixi P/N 50889. The x-ray generator system (3) (Lixi P/N 47263), of the preferred embodiment is capable of producing 70 k-V at 100 micro amps. When the x-ray generator is activated, x-rays pass through the sample and are detected and magnified via an image detector (4), Lixi P/N D-708 for one inch field of view or P/N D-709 for a 2 inch field of view, connected to a high resolution CCTV system (5) (Lixi P/N 51999). A charge coupled device (CCD) camera can be connected to an imaging system as found in the Lixi 2001 model or any image processing system capable of processing pixel-based images. The camera can be connected to a color image enhancer (6), such as Lixi P/N 52025. The image processor can also be coupled with a personal computer using window-based software (7) (here, Lixi P/Ns 50924 and 52058). The output can be received on a color monitor (8) such as Lixi P/N 52026, or a black and white video printer (9), such as Lixi P/N 50887, or a standard video cassette recorder. The contact lens mold assembly is then examined for a variety of characteristics, such as edge quality, alignment fit, center thickness, prism, etc.

The term "proper edge alignment" is defined herein as the condition where the front curve portion of the mold assembly and the base curve portion of the mold assembly are each properly seated to produce a coherent edge in the resulting contact lens. Poor edge alignment usually results in a defective edge on the contact lens or exhibits itself in other defective surface attributes of the lens. "Alignment gap" (12, FIG. 2), is defined as the cavity formed by the seating of the male member (10, FIG. 2) into the female member (11, FIG. 2).

As used herein, the term "edge quality" is defined as the physical configuration of the mating of the base curve and front curve portions of the mold assembly. As the component is imaged using the x-ray system, it can be clearly viewed as either a continuous edge or one in which the edge has physical deformations.

As used herein, the term "center thickness" refers to the distance from the base curve portion of the mold assembly to the front curve portion based on the image received on the interior of the casting cup and compared to a fixed standard pin (for standard reference measurement) located on the stainless steel holder upon which the cup is placed. Center thickness values typically range from 20–200 microns, but can vary with design. Edge thickness is defined as the cross-sectional distance as measured at any point up to 0.5 mm from the apex of the edge. The maximum value of the edge thickness is about 0.2 mm, but can vary with the design.

Many modifications and variations of the present invention can be made without departing from its spirit and scope, as will become apparent to one of ordinary skill in the art. The specific embodiments described herein are offered by way of example only, and the invention should not be construed as limited thereby.

What is claimed is:

1. A process for imaging a contact lens casting cup assembly which comprises transmitting x-rays through the contact lens casting cup assembly and then onto an image sensing means.

2. The process according to claim 1, wherein the process further comprises fixing an image produced by said image sensing means through use of a printer.

3. The process according to claim 1, wherein the process further comprises the step of displaying an image produced by said image sensing means using a television camera, which displays said image on a video monitor.

4. The process according to claim 1, wherein the process further comprises the step of measuring internal dimensions of the contact lens casting cup assembly.

5. The process according to claim 4, wherein the step of measuring the internal dimensions of the contact lens casting cup assembly comprises using a microfocus x-ray source having (a) a target size ranging from 10–15 microns and (b) an x-ray tube designed to convert electrical energy into radiation.

6. The process according to claim 1, wherein the process further comprises the step of non-destructively inspecting edge alignment fit of the contact lens casting cup assembly.

7. The process according to claim 6, wherein the process further comprises the step of non-destructively measuring center thickness of said contact lens casting cup assembly.

8. The process according to claim 6, wherein the process further comprises the step of non-destructively measuring alignment gap of said contact lens casting cup assembly.

9. The process according to claim 6, wherein the process further comprises the step of non-destructively measuring edge thickness of said contact lens casting cup assembly.

* * * * *